United States Patent
Barham

(10) Patent No.: US 7,667,101 B2
(45) Date of Patent: Feb. 23, 2010

(54) WATERMELON LINE 110-1005

(75) Inventor: Robert Barham, Gilroy, CA (US)

(73) Assignee: Seminis Vegetable Seeds, Inc., Woodland, CA (US)

(*) Notice: Subject to any disclaimer, the term of this patent is extended or adjusted under 35 U.S.C. 154(b) by 0 days.

(21) Appl. No.: 12/014,637

(22) Filed: Jan. 15, 2008

(65) Prior Publication Data
US 2008/0244764 A1    Oct. 2, 2008

Related U.S. Application Data

(60) Provisional application No. 60/885,448, filed on Jan. 18, 2007.

(51) Int. Cl.
*A01H 1/00* (2006.01)
*A01H 5/00* (2006.01)
*A01H 5/10* (2006.01)
*C12N 5/04* (2006.01)
*C12N 15/82* (2006.01)

(52) U.S. Cl. .................... 800/308; 435/410; 435/6; 800/260; 800/278

(58) Field of Classification Search ............ None
See application file for complete search history.

(56) References Cited

U.S. PATENT DOCUMENTS

| | | | |
|---|---|---|---|
| 6,355,865 B1 * | 3/2002 | Elmstrom | 800/274 |
| 6,747,191 B2 * | 6/2004 | Zhang | 800/308 |
| 7,115,800 B2 | 10/2006 | Barham et al. | 800/308 |
| 2007/0011784 A1 | 1/2007 | Barham et al. | 800/308 |

FOREIGN PATENT DOCUMENTS

WO   WO 2006/014463   2/2006

OTHER PUBLICATIONS

Karchi et al (1981, HortSci. 16:573).*
Layton (1976, PVP No. 7500053).*
Edelstein et al, 2002, HortSci. 37:981-983.*
Hashizume et al (2003, Theor. Appl. Genet. 106:779-785).*
Mexican Application for the Title of Obtainer No. 821 for Watermelon Variety TCS1101005, dated Nov. 21, 2007.

* cited by examiner

*Primary Examiner*—Anne Kubelik
(74) *Attorney, Agent, or Firm*—Alissa Eagle, Esq.; Sonnenschein Nath & Rosenthal LLP

(57) ABSTRACT

The invention provides seed and plants of the watermelon line designated 110-1005. The invention thus relates to the plants, seeds and tissue cultures of watermelon line 110-1005, and to methods for producing a watermelon plant produced by crossing a plant of watermelon line 110-1005 with itself or with another watermelon plant, such as a plant of another line. The invention further relates to seeds and plants produced by such crossing. The invention further relates to parts of a plant of watermelon line 110-1005, including the fruit and gametes of such plants.

30 Claims, No Drawings

WATERMELON LINE 110-1005

This application claims the priority of U.S. Provisional Application Ser. No. 60/885,448, filed Jan. 18, 2007, the entire disclosure of which is specifically incorporated herein by reference.

BACKGROUND OF THE INVENTION

1. Field of the Invention

The present invention relates to the field of plant breeding and, more specifically, to the development of watermelon line 110-1005.

2. Description of Related Art

Watermelons are natural diploids, referred to as 2N (N=1), with chromosomes arranged in pairs. Many plants, including watermelons, can undergo a duplication of their entire set of chromosomes and exist as tetraploids, referred to as 4N (4N=44). Watermelon tetraploids can be produced routinely in the laboratory using cell biology techniques.

A tetraploid (4N) female parent can be crossed with a diploid (2N) male parent to produce triploid (3N) seeds (3N=33). A hybrid triploid plant produces watermelon fruit which is seedless. Although triploid plants do not usually produce any viable seed, small, white, rudimentary seeds may develop within the fruit and can be eaten with the fruit, as in the case of parthenocarpic cucumber. The number and size of the white, rudimentary seeds varies with the variety. Occasionally a dark, hard seedcoat or a true seed may be found in a triploid watermelon.

A tetraploid seed parent typically produces only 5 to 10% as many seeds as a typical diploid plant. Commercial seed production of a triploid hybrid cultivar requires a substantial amount of seed for a commercially viable product.

Tetraploid parental lines generally have a uniform or "solid" colored rind, i.e., a rind pattern that is primarily one color as opposed to a rind pattern having striping. Generally, the rind of the fruit from tetraploid parental lines has a light green to a creamy green color. This color is also sometimes referred to as "gray."

There remains a need for improved tetraploid watermelon lines with good yield of both triploid and tetraploid seeds and which can be used to produce triploid fruit which have traits such as, for example, a small size, dark stripes or a blocky shape without end tapering.

SUMMARY OF THE INVENTION

In one aspect, the present invention provides a watermelon plant of the line designated 110-1005. Also provided are watermelon plants having all the physiological and morphological characteristics of the watermelon line designated 110-1005. Parts of the watermelon plant of the present invention are also provided, for example, including pollen, an ovule, a fruit, and a cell of the plant.

The invention also concerns seed of watermelon line 110-1005. The watermelon seed of the invention may be provided as an essentially homogeneous population of watermelon seed of the line designated 110-1005. Essentially homogeneous populations of seed are generally free from substantial numbers of other seed. Therefore, seed of line 110-1005 may be defined as forming at least about 97% of the total seed, including at least about 98%, 99% or more of the seed. The population of watermelon seed may be particularly defined as being essentially free from hybrid seed. The seed population may be separately grown to provide an essentially homogeneous population of watermelon plants designated 110-1005.

In another aspect of the invention, a plant of watermelon line 110-1005 comprising an added heritable trait is provided. The heritable trait may comprise a genetic locus that is, for example, a dominant or recessive allele. In one embodiment of the invention, a plant of watermelon line 110-1005 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of line 110-1005 is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of the line 110-1005 include those traits set forth in the tables herein, and include for example, yield, maturity, and fruit quality. The regenerable cells in such tissue cultures may be derived from embryos, meristems, cotyledons, pollen, leaves, anthers, roots, root tips, pistil, flower, seed and stalks. Still further, the present invention provides watermelon plants regenerated from a tissue culture of the invention, the plants having all the physiological and morphological characteristics of line 110-1005.

In yet another aspect of the invention, processes are provided for producing watermelon seeds, plants and fruit, which processes generally comprise crossing a first parent watermelon plant with a second parent watermelon plant, wherein at least one of the first or second parent watermelon plants is a plant of the line designated 110-1005. These processes may be further exemplified as processes for preparing hybrid watermelon seed or plants, wherein a first watermelon plant is crossed with a second watermelon plant of a different, distinct line to provide a hybrid that has, as one of its parents, the watermelon plant line 110-1005. In these processes, crossing will result in the production of seed. The seed production occurs regardless of whether the seed is collected or not.

In one embodiment of the invention, the first step in "crossing" comprises planting seeds of a first and second parent watermelon plant, often proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent watermelon plants into plants that bear flowers. A third step may comprise preventing self-pollination of the plants, such as by emasculating the male portions of flowers, (i.e., treating or manipulating the flowers to produce an emasculated parent watermelon plant). Self-incompatibility systems may also be used in some hybrid crops for the same purpose. Self-incompatible plants still shed viable pollen and can pollinate plants of other varieties but are incapable of pollinating themselves or other plants of the same line.

A fourth step for a hybrid cross may comprise cross-pollination between the first and second parent watermelon plants.

Yet another step comprises harvesting the seeds or from at least one of the parent watermelon plants. The harvested seed can be grown to produce a watermelon plant or hybrid watermelon plant.

The present invention also provides the watermelon seeds and plants produced by a process that comprises crossing a first parent watermelon plant with a second parent watermelon plant, wherein at least one of the first or second parent watermelon plants is a plant of the line designated 110-1005. In one embodiment of the invention, watermelon seed and plants produced by the process are first generation ($F_1$) hybrid watermelon seed and plants produced by crossing a plant in accordance with the invention with another, distinct plant. The present invention further contemplates plant parts of such an $F_1$ hybrid watermelon plant, and methods of use thereof. Therefore, certain exemplary embodiments of the invention provide an $F_1$ hybrid watermelon plant and seed thereof.

In still yet another aspect of the invention, the genetic complement of the watermelon plant line designated 110-1005 is provided. The phrase "genetic complement" is used to refer to the aggregate of nucleotide sequences, the expression of which sequences defines the phenotype of, in the present case, a watermelon plant, or a cell or tissue of that plant. A genetic complement thus represents the genetic makeup of a cell, tissue or plant, and a hybrid genetic complement represents the genetic make up of a hybrid cell, tissue or plant. The invention thus provides watermelon plant cells that have a genetic complement in accordance with the watermelon plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line 110-1005 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by watermelon plant cells, tissues, plants, and seeds, formed by the combination of a haploid genetic complement of a watermelon plant of the invention with a haploid genetic complement of a second watermelon plant, preferably, another, distinct watermelon plant. In another aspect, the present invention provides a watermelon plant regenerated from a tissue culture that comprises a hybrid genetic complement of this invention.

In still yet another aspect, the invention provides a plant of a tetraploid inbred watermelon line that exhibits an average triploid seed yield of at least 34 seeds per tetraploid fruit produced by using the line as a seed parent with a diploid pollen donor plant. In certain embodiments, the trait may be defined as controlled by genetic means for the expression of the trait found in watermelon line 110-1005. In specific embodiments, the seed yield may be further defined as, for example, at least about 50, at least about 75, at least about 100, at least about 125 or at least about 150 seeds per tetraploid fruit, including from about 50 to about 150, from about 34 to about 100, and from about 60 to about 120 seeds per tetraploid fruit produced by using a plant of the line as a seed parent with a diploid pollen donor plant. In one non-limiting embodiment, the diploid pollen donor plant may be a publicly available line, such as any of the lines Crimson Sweet; Jubilee, Sugar Baby, Dixie Lee, or All Sweet.

In still yet another aspect, the present invention provides a method of producing a watermelon plant derived from the watermelon line 110-1005, the method comprising the steps of: (a) preparing a progeny plant derived from watermelon line 110-1005, wherein said preparing comprises crossing a plant of the watermelon line 110-1005 with a second watermelon plant; (b) crossing the progeny plant with itself or a second plant to produce a seed of a progeny plant of a subsequent generation; (c) growing a progeny plant of a subsequent generation from said seed of a progeny plant of a subsequent generation and crossing the progeny plant of a subsequent generation with itself or a second plant; and (d) repeating steps (b) and (c) for an additional 3-10 generations to produce a watermelon plant derived from watermelon line 110-1005. The plant derived from watermelon line 110-1005 may be an inbred line, and step (d) may be defined as comprising sufficient inbreeding to produce the inbred line. In the method, it may be desirable to select particular plants resulting from step (c) for continued crossing according to steps (b) and (c). By selecting plants having one or more desirable traits, a watermelon plant derived from the watermelon line 110-1005 is obtained which possesses some of the desirable traits of watermelon line 110-1005 as well potentially other selected traits.

In certain embodiments, the present invention provides a method of producing watermelon comprising: (a) cultivating a plant of watermelon line 110-1005 to maturity and (b) obtaining at least a first watermelon from the plant.

These and other features and advantages of this invention are described in, or are apparent from, the following detailed description of various exemplary embodiments of the devices and methods according to this invention.

DETAILED DESCRIPTION OF THE INVENTION

The instant invention provides methods and compositions relating to plants, seeds and derivatives of watermelon line 110-1005. Watermelon line 110-1005 is a tetraploid line and is particularly useful for crossing with a diploid watermelon parent to produce triploid watermelon. Line 110-1005 is useful for producing fruit which has unique and desirable physiological and morphological characteristics. Line 110-1005 can be used to obtain fruit which has green striping and improved seed yield of both tetraploid and triploid seeds. In addition, line 110-1005 produces watermelon fruit which is of a "blocky" shape. The fruit may vary in size depending on environmental conditions; however, the length/width ratio is typically between approximately 1.35 to approximately 1.40.

A. Origin and Breeding History of Tetraploid Line 110-1005

In Year 1, Diploid watermelon Calsweet was converted into a tetraploid using treatment with colchicine. In particular, 0.5% aqueous colchicine was applied to the apical meristem of Calsweet watermelon seedlings at the cotyledon state of growth on each of three mornings. The surviving plants were transplanted to the field and self pollinated. The initial tetraploid line obtained was identified as B125. B125 produced fruit which was blocky in shape and had green striping. However, the triploid seed yield of fruit produced from tetraploid line B125 was poor. The triploid seed yield, using line B125 as the female parent with various diploid male parents, ranged between two and seventeen triploid seeds on average per fruit. (See Table 2, below).

Line B125 was self pollinated in Year 1 and Year 2 and was open pollinated in Year 3 and Year 4. In Year 5, non-striped segregants were noted, indicating outcrossing between B125 and a non-striped tetraploid in Year 3. Each year between Year 5 and Year 13, starting with the lines developed from the open pollinated fruits, plants were self pollinated and selected for seed setting and fruit type of blocky shape and wide, dark green stripes. In Year 13, line 110-1005 was sufficiently uniform to bulk the self pollinated fruit.

B. Physiological and Morphological Characteristics of Watermelon Line

In accordance with one aspect of the present invention, there is provided a plant having the physiological and morphological characteristics of watermelon line 110-1005. The tetraploid line 110-1005 produces fruit which is "blocky" in shape and medium in size. Blocky is defined as an intermediate fruit shape between long and round and generally includes fruit which has a length to width ratio of approximately 1.25 to approximately 1.7. In contrast, a round watermelon generally has a length to width ratio of approximately 1.25 or less and a long watermelon has a length to width ratio of approximately 1.7 or higher. A medium watermelon generally has an average weight between approximately 12 pounds and approximately 16 pounds. In contrast, a small or "personal sized" watermelon generally has an average weight of approximately 12 pounds or less, a medium-large watermelon generally has an average weight between approximately 14 pounds and 17 pounds and a large watermelon has an average weight of approximately 16 pounds or more. A description of the physiological and morphological characteristics of watermelon line 110-1005 is presented in Table 1.

TABLE 1

Physiological and Morphological Characteristics of Line 110-1005

| CHARACTERISTIC | 110-1005 |
|---|---|
| 1. Type | Oblong |
| 2. Area of Best Adaptation | Most Areas |
| 3. Emergence to Anthesis | |
| No. of Days Later Than Charleston Grey | 3 |
| 4. Pollination to Maturity | |
| No. of Days Later Than Charleston Grey | 3 |
| 5. Ploidy | Tetraploid |
| 6. Plant | Monoecious |
| Cotyledon | Flat |
| No. of Flowers per Plant at First Fruit Set: | |
| Staminate | 20 |
| Pistillate | 1 |
| Perfect | 0 |
| No. of Main Stems at Crown | 5 |
| 7. Stem | Round, 20 mm Diameter at Second Node, Pubescent |
| cm vine length ÷ no. of internodes (at last harvest) | 10 |
| 8. Leaf | obovate shape and longer than wide |
| Dorsal Surface | Smooth |
| Ventral Surface | Pubescent |
| Color | Medium Green |
| 9. Flower | |
| Staminate | 4 cm across |
| Pistillate | 4 cm across |
| Color | yellow |
| 10. Mature Fruit | |
| Shape | oval |
| Length | 30 cm |
| Diameter at Midsection | 22 cm |

TABLE 1-continued

Physiological and Morphological Characteristics of Line 110-1005

| CHARACTERISTIC | 110-1005 |
|---|---|
| Average Weight | 7 kg |
| Length ÷ Diameter × 10 | 13 |
| Texture | smooth |
| Color pattern | stripe |
| Primary Color | light green (Charleston Grey) |
| Secondary Color (refers to stripes) | dark Green (Florida Giant) |
| 11. Rind | Tough |
| Thickness at blossom end | 10 mm |
| Thickness at sides | 15 mm |
| 12. Flesh | |
| Texture | Crisp and Fine (little fiber) |
| Color | Dark Red |
| Hollow Heart | 3% |
| Placental Separation | 1% |
| Transverse Crack | 0% |
| 13. Seed | |
| Length | 12 mm |
| Width | 7 mm |
| Thickness | 3 mm |
| Length ÷ Width × 10 | 17 mm |
| Weight Per 1000 Seeds | 65 gm |
| Average No. Seed Per Fruit | 100 |
| Color | Dark Brown Mottled |
| 14. Disease Resistance | |
| Gummy Stem Blight | Susceptible |
| Watermelon Mosaic | Susceptible |
| Powdery Mildew | Susceptible |
| Cucumber Mosaic | Resistant |
| 15. Other Resistance | |
| Hollow Heart | Resistant |

*These are typical values. Values may vary due to environment. Other values that are substantially equivalent are within the scope of the invention.

Line 110-1005 produces fruit which are uniform and stable within the limits of environmental influence for all of the traits as described herein. Line 110-1005 has been self-pollinated and planted for a number of generations to produce the homozygosity and phenotypic stability to make this line useful in commercial hybrid seed production. No variant traits have been observed or are expected for this line.

Tetraploid line 110-1005 provides sufficient tetraploid and triploid seed yield. Tetraploid watermelon line 110-1005, being substantially homozygous, can be reproduced by planting seeds of the line, growing the resulting watermelon plant under self-pollinating or sib-pollinating conditions and harvesting the resulting seeds using techniques familiar to one of skill in the art.

C. Breeding Watermelon Line 110-1005

One aspect of the current invention concerns methods for crossing the watermelon line 110-1005 with itself or a second plant and the seeds and plants produced by such methods. These methods can be used for propagation of line 110-1005, or can be used to produce hybrid triploid watermelon seeds and the plants grown therefrom. Hybrid triploid seeds are produced by crossing line 110-1005 with a diploid watermelon parent line. The watermelon seeds can be used by farmers in the commercial production of watermelons.

Triploid watermelon seeds and plants produced from an inbred tetraploid watermelon parent 110-1005 comprise three sets of alleles, two sets of alleles are the same as line 110-1005, with one additional set of alleles derived from the diploid watermelon male parent line.

The line of the present invention can be used for the development of new triploids based on the elite nature of the genetic background of the line. In selecting a second plant to cross with 110-1005 for the purpose of developing novel watermelon varieties, it will typically be preferred to choose those plants which either themselves exhibit one or more selected desirable characteristics or which exhibit the desired characteristic(s) when in hybrid combination. Examples of desirable characteristics include seed yield, germination, fruit size, fruit shape, rind coloring/striping, color of fruit flesh, seedling vigor, maturity, fruit yield, ease of fruit setting, disease tolerance and adaptability for soil and climate conditions.

Tetraploid line 110-1005 can be used as a female parent to cross with a diploid watermelon plant, the male parent. Triploid seed yield, using line 110-1005 as the female parent with various diploid (2N) male parents, ranged between 47 and 161 triploid seeds on average per fruit (see Table 2).

TABLE 2

Performance analysis of triploid hybrid progeny produced using line 110-1005 as one parent

| Hybrid* | Female Parent | # Fruits | # Seeds | Average # Seeds/Fruit |
|---------|---------------|----------|---------|----------------------|
| A | B 125 | 1 | 2 | 2 |
| B | B 125 | 1 | 7 | 7 |
| C | B 125 | 1 | 17 | 17 |
| D | 110-1005 | 4 | 486 | 121 |
| E | 110-1005 | 2 | 323 | 161 |
| F | 110-1005 | 5 | 486 | 97 |
| G | 110-1005 | 38 | 3537 | 93 |
| H | 110-1005 | 29 | 3268 | 113 |
| I | 110-1005 | 13 | 1000 | 77 |
| J | 110-1005 | 10 | 927 | 93 |
| K | 110-1005 | 7 | 683 | 98 |
| L | 110-1005 | 23 | 1194 | 52 |
| M | 110-1005 | 32 | 1091 | 34 |
| N | 110-1005 | 25 | 1172 | 47 |
| O | 110-1005 | 29 | 1532 | 53 |
| P | 110-1005 | 25 | 1321 | 53 |
| Q | 110-1005 | 33 | 1542 | 47 |
| R | 110-1005 | 22 | 1486 | 68 |
| S | 110-1005 | 17 | 986 | 58 |
| T | 110-1005 | 10 | 819 | 82 |

*Each letter represents a unique combination.

The blocky shape and medium size of fruit produced by inbred tetraploid 110-1005 allows for the development of fruit of a desired size and shape from within a broad range of sizes and shapes. The tetraploid line 110-1005 can beneficially be used as the female parent in combination with a male parent chosen for its fruit shape (round, blocky or long) and/or fruit size (small, medium or large) to produce a triploid hybrid plant with fruit of the desired shape and size. A male parent with the same shape and size characteristics as are found in inbred tetraploid female parent 110-1005 will result in triploid hybrid plants which can be expected to produce watermelon fruits of a similar shape and size to inbred tetraploid female parent 110-1005. Alternatively, the male parent can be chosen with differing characteristics from 110-1005 to produce triploid fruit in varying combinations of shape and/or size. See Table 3, which shows progeny produced using line 110-1005 as one parent. For example, a small fruited diploid male can be used to produce a "personal" sized triploid hybrid or a long-fruited male can be used to produce a long triploid hybrid. Other combinations would be apparent to one of skill in the art.

TABLE 3

Fruit characteristics of progeny produced using line 110-1005 as one parent

| Tetraploid Parent | Fruit Shape/Size of Diploid Parent* | Fruit Shape of Triploid Hybrid | Fruit Size of Triploid Hybrid |
|-------------------|-------------------------------------|--------------------------------|-------------------------------|
| 110-1005 | Blocky, Large | Blocky | Medium-large |
| 110-1005 | Blocky, Large | Blocky | Medium-large |
| 110-1005 | Round, Small | round/oval | Small |
| 110-1005 | Round, Small | round/oval | Small |
| 110-1005 | Elongated, Small | elongated | Small |
| 110-1005 | Round, Medium | round/oval | Medium |
| 110-1005 | Elongated, Large | elongated | Large |
| 110-1005 | Round, Small | round/oval | Medium |
| 110-1005 | Round, Medium | round/oval | Medium |
| 110-1005 | Round, Small | round/oval | Medium |
| 110-1005 | Round, Small | round/oval | Medium |
| 110-1005 | Round, Small | round/oval | Medium |
| 110-1005 | Round, Small | round/oval | Medium |
| 110-1005 | Round, Small | round/oval | Medium |
| 110-1005 | Round, Small | round/oval | Medium |
| 110-1005 | Round, Small | round/oval | Large |
| 110-1005 | Round, Medium | round/oval | Medium |
| 110-1005 | Round, Large | round/oval | Medium |
| 110-1005 | Elongated, Large | elongated | Medium-large |
| 110-1005 | Round, Large | round/oval | Medium |
| 110-1005 | Round, Large | round/oval | Medium |
| 110-1005 | Round, Large | round/oval | Medium |
| 110-1005 | Round, Large | round/oval | Medium |
| 110-1005 | Round, Large | round/oval | Medium |
| 110-1005 | Round, Large | round/oval | Medium |
| 110-1005 | Round, Large | round/oval | Medium |
| 110-1005 | Round, Large | round/oval | Medium |
| 110-1005 | Round, Large | round/oval | Medium |
| 110-1005 | Round, Large | round/oval | Medium |
| 110-1005 | Round, Large | round/oval | Medium |
| 110-1005 | Round, Large | round/oval | Medium |
| 110-1005 | Round, Large | round/oval | Medium |

*Each row is a unique diploid parent line.

The tetraploid line 110-1005 produces plants having fruit which has a green rind and visible striping independent of the male line chosen. Since it is often preferable for the fruit to have dark green striping, often the male diploid parent is chosen to have similar color characteristics to line 110-1005.

The tetraploid line 110-1005 produces fruit with a deep red color of fruit flesh. This is generally preferred and the diploid parent can be chosen to produce triploid hybrid fruit with the same characteristics.

Watermelon line 110-1005 can be crossed with a different variety to produce first generation ($F_1$) watermelon progeny. The hybrid progeny are produced regardless of characteristics of the two varieties produced. As such, an $F_1$ hybrid watermelon plant may be produced by crossing 110-1005 with any second watermelon plant. The second watermelon plant may be genetically homogeneous (e.g., inbred) or may itself be a hybrid. Therefore, any $F_1$ hybrid watermelon plant produced by crossing watermelon line 110-1005 with a second watermelon plant is a part of the present invention.

The tetraploid line 110-1005 can also be used in the commercial production of triploid watermelon seed. In the production of triploid seed, the tetraploid and diploid parental lines are planted in the same field. Cross-pollination between the tetraploid line, the female parental line of the triploid hybrid seed, and the diploid line, the male parental line, can be accomplished by either natural or mechanical techniques. Natural pollination occurs in watermelon either by self pollination or natural cross pollination, which typically is aided by pollinating organisms. In either natural or artificial crosses, flowering and flowering time are important considerations. Triploid watermelon seeds are produced only in watermelons of tetraploid plants that are fertilized with pollen of diploid plants. Tetraploid line 110-1005 can be used in combination with any of the known diploid lines to produced triploid watermelon.

The unique traits of 110-1005 make it useful as a parental line in the development of new tetraploid inbreds. Line 110-1005 can be used as either a female or male parent to cross with another inbred or hybrid tetraploid watermelon plant to develop new tetraploid inbreds. In one embodiment, a 110-1005 plant is crossed with another tetraploid watermelon plant and progeny seed is collected and grown. Further crosses can then be made as determined by a breeder of skill in the art. Progeny plants comprise certain alleles of 110-1005, as described above.

When the term watermelon line 110-1005 is used in the context of the present invention, this also includes plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those watermelon plants which are developed by a plant breeding technique called backcrossing, wherein essentially all of the desired morphological and physiological characteristics of a variety are recovered in addition to the single locus transferred into the variety via the backcrossing technique. Backcrossing methods can be used with the present invention to improve or introduce a characteristic into the present variety. The parental watermelon plant which contributes the locus for the desired characteristic is termed the nonrecurrent or donor parent. This terminology refers to the fact that the nonrecurrent parent is used one time in the backcross protocol and therefore does not recur. The parental watermelon plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (non-recurrent parent) that carries the single locus of interest to be transferred. The resulting progeny from this cross are then crossed again to the recurrent parent and the process is repeated until a watermelon plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny tetraploid watermelon plants of a backcross in which 110-1005 is the recurrent parent comprise (i) the desired trait from the non-recurrent parent and (ii) all of the physiological and morphological characteristics of tetraploid watermelon line 110-1005 as determined at the 5% significance level when grown in the same environmental conditions.

Watermelon varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, enhanced nutritional quality, yield stability, and yield enhancement. These comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of watermelon plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of watermelon are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

D. Plants Derived from Watermelon Line 110-1005 by Genetic Engineering

Many useful traits that can be introduced by backcrossing, as well as directly into a plant, are those which are introduced by genetic transformation techniques. Genetic transformation may therefore be used to insert a selected transgene into the watermelon line of the invention or may, alternatively, be used for the preparation of transgenes which can be introduced by backcrossing. Methods for the transformation of plants, including watermelon, are well known to those of skill in the art. Techniques which may be employed for the genetic transformation of watermelon include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. Microprojectile bombardment techniques are widely applicable, and may be used to transform virtually any plant species. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target watermelon cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of watermelon plants and expression of foreign genetic elements is exemplified in Choi et al., Genetic transformation and plant regeneration of watermelon using *Agrobacterium tumefaciens*, Plant Cell Rep 13: 344-348 (1994), and Ellul et al., The expression of the *Saccharomyces cerevisiae* HAL1 gene increases salt tolerance in transgenic watermelon [*Citrullus lanatus* (Thunb.) Matsun. & Nakai.], Theor Appl Genet. 107: 462-469 (2003).

A number of promoters have utility for plant gene expression for any gene of interest including but not limited to selectable markers, scoreable markers, genes for pest tolerance, disease tolerance, nutritional enhancements and any other gene of agronomic interest. Examples of constitutive promoters useful for watermelon plant gene expression include, but are not limited to, the cauliflower mosaic virus (CaMV) P-35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); a tandemly duplicated version of the CaMV 35S promoter, the enhanced 35S promoter (P-e35S) the nopaline synthase promoter (An et al., Plant Physiol. 88:547, 1988), the octopine synthase promoter (Fromm et al., Plant Cell 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wun1, Siebertz et al., Plant Cell 1:961, 1989); or (5) chemicals such as methyl jasmonate, salicylic acid, or Safener. It may also be advantageous to employ organ-specific promoters (e.g., Roshal et al., EMBO J. 6:1155, 1987; Schernthaner et al., EMBO J. 7:1249, 1988; Bustos et al., Plant Cell 1:839, 1989).

Exemplary nucleic acids which may be introduced to the watermelon lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a watermelon plant according to the invention. Non-limiting examples of particular genes and corresponding phenotypes one may choose to introduce into a watermelon plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev. 9:207, 1991). The RNA could also be a catalytic RNA molecule (i.e., a ribozyme) engineered to cleave a desired endogenous mRNA product (see for example, Gibson and Shillito, Mol. Biotech. 7:125, 1997). Thus, any gene which produces a protein or mRNA which expresses a phenotype or morphology change of interest is useful for the practice of the present invention.

Definitions

In the description and tables herein, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor conferring male sterility or a chemical agent.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Maturity Date: Fruit is considered mature when it has a brix reading of between approximately 8 and 10.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a watermelon variety are recovered in addition to the characteristics of the single locus transferred into the variety via the backcrossing technique and/or by genetic transformation.

Substantially Equivalent: A characteristic that, when compared, does not show a statistically significant difference (e.g., $p=0.05$) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a watermelon plant by transformation.

Triploid: A cell or organism having three sets of chromosomes.

Deposit Information

A deposit of watermelon line 110-1005, disclosed above and recited in the claims, has been made with the American Type Culture Collection (ATCC), 10801 University Blvd., Manassas, Va. 20110-2209. The date of deposit was Oct. 31, 2006. Upon issuance of a patent, all restrictions upon the deposit will be removed, and the deposit is intended to meet all of the requirements of 37 C.F.R. §1.801-1.809. The accession number for those deposited seeds of watermelon line 110-1005 is ATCC Accession No. PTA-7957. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997.
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 1 8:6531-6535, 1990.
WO 99/31248

What is claimed is:

1. A seed of a watermelon line 110-1005, wherein a sample of the seed of watermelon line 110-1005 was deposited under ATCC Accession Number PTA-7957.

2. A plant of watermelon line 110-1005, wherein a sample of the seed of watermelon line 110-1005 was deposited under ATCC Accession Number PTA-7957.

3. A plant part of the plant of claim 2.

4. The plant part of claim 3, wherein said part is selected from the group consisting of a fruit, pollen, an ovule and a cell.

5. A watermelon plant, or a part thereof, having all the physiological and morphological characteristics of the watermelon plant of claim 2.

6. A tissue culture of regenerable cells of watermelon line 110-1005, wherein a sample of the seed of watermelon line 110-1005 was deposited under ATCC Accession Number PTA-7957.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A watermelon plant regenerated from the tissue culture of claim 6, wherein the regenerated plant expresses all of the physiological and morphological characteristics of watermelon line 110-1005, wherein a sample of the seed of watermelon line 110-1005 was deposited under ATCC Accession Number PTA-7957.

9. A method of producing watermelon seed, said method comprising crossing a plant of watermelon line 110-1005 with a second watermelon plant, wherein a sample of the seed of watermelon line 110-1005 was deposited under ATCC Accession Number PTA-7957.

10. The method of claim 9, wherein said second watermelon plant is diploid.

11. The method of claim 9, wherein said second watermelon plant is tetraploid.

12. The method of claim 9, wherein the plant of watermelon line 110-1005 is the female parent.

13. An F1 hybrid seed produced by the method of claim 9.

14. An F1 hybrid plant produced by growing the seed of claim 13.

15. A method for producing a seed of a line 110-1005-derived watermelon plant, said method comprising the steps of:
   (a) crossing a watermelon plant of line 110-1005 with a second watermelon plant, wherein a sample of the seed of watermelon line 110-1005 was deposited under ATCC Accession Number PTA-7957; and
   (b) allowing seed of a 110-1005-derived watermelon plant to form.

16. The method of claim 15, further comprising the steps of:
   (c) crossing a plant grown from said 110-1005-derived watermelon seed with itself or a second watermelon plant to yield additional 110-1005-derived watermelon seed;
   (d) growing said additional 110-1005-derived watermelon seed of step (c) to yield additional 110-1005-derived watermelon plants; and
   (e) repeating the crossing and growing steps of (c) and (d) to generate further 110-1005-derived watermelon plants.

17. A method of producing a watermelon plant derived from line 110-1005, said method comprising the steps of:
   (a) growing a diploid reversion of a watermelon plant of line 110-1005, wherein a sample of the seed of watermelon line 110-1005 was deposited under ATCC Accession Number PTA-7957;
   (b) allowing said diploid watermelon plant to self-pollinate; and
   (c) harvesting seed from said diploid watermelon plant.

18. The method of claim 17, further comprising the step of:
   (d) crossing said diploid watermelon plant with itself or another diploid watermelon plant to yield additional 110-1005-derived diploid watermelon seed;
   (e) growing said diploid 110-1005-derived watermelon seed of step (d) to yield additional 110-1005-derived watermelon plants; and
   (f) repeating the crossing and growing steps of (d) and (e) to generate further 110-1005-derived diploid watermelon plants.

19. The method of claim 17, further comprising doubling the chromosome number of said diploid watermelon plant to produce a tetraploid watermelon plant.

20. A method of vegetatively propagating a plant of watermelon line 110-1005, said method comprising the steps of:
(a) collecting shoot tissue of a watermelon plant according to claim 2;
(b) cultivating said tissue to obtain proliferated shoots; and
(c) rooting said proliferated shoots to obtain rooted plantlets.

21. The method of claim 20, further comprising growing plants from said rooted plantlets.

22. A method of introducing a desired trait into tetraploid watermelon line 110-1005, said method comprising:
(a) crossing a plant of line 110-1005 with a second watermelon plant that comprises a desired trait to produce F1 progeny, wherein a sample of the seed of watermelon line 110-1005 was deposited under ATCC Accession Number PTA-7957;
(b) selecting an F1 progeny that comprises the desired trait;
(c) crossing the selected F1 progeny with a plant of line 110-1005 to produce backcross progeny;
(d) selecting backcross progeny comprising the desired trait and the physiological and morphological characteristic of watermelon line 110-1005; and
(e) repeating steps (c) and (d) three or more times in succession to produce selected fourth or higher backcross progeny that comprise the desired trait and all of the physiological and morphological characteristics of tetraploid watermelon line 110-1005 when grown in the same environmental conditions.

23. A watermelon plant produced by the method of claim 22.

24. A method of producing a plant of watermelon line 110-1005 comprising an added desired trait, the method comprising introducing a transgene conferring the desired trait into a plant of watermelon line 110-1005, wherein a sample of the seed of watermelon line 110-1005 was deposited under ATCC Accession Number PTA-7957.

25. A progeny plant of the plant of claim 1 that comprises all of the physiological and morphological characteristics of watermelon line 110-1005, wherein a sample of the seed of watermelon line 110-1005 was deposited under ATCC Accession Number PTA-7957.

26. The plant of claim 25, wherein the seed yield of the plant is at least 50 seeds per tetraploid fruit produced by using the line as a seed parent with a diploid pollen donor plant.

27. A seed that produces the plant of claim 25.

28. A method of determining the genotype of a plant of watermelon line 110-1005, said method comprising detecting in the genome of the plant a plurality of polymorphisms, wherein a sample of the seed of watermelon line 110-1005 was deposited under ATCC Accession Number PTA-7957.

29. The method of claim 28, further comprising the step of storing the results of the step of detecting the plurality of polymorphisms on a computer readable medium.

30. A method of producing watermelon, said method comprising:
(a) cultivating the plant of claim 2 to maturity, and
(b) obtaining at least a first watermelon from the plant.

* * * * *